United States Patent
Cooper et al.

[11] Patent Number: 4,963,560
[45] Date of Patent: Oct. 16, 1990

[54] 1,4-DIHYDROPYRIDINE DERIVATIVES

[75] Inventors: Kelvin Cooper; Michael J. Fray; Kenneth Richardson; John Steele, all of Deal, England

[73] Assignee: Pfizer Inc., New York, N.Y.

[21] Appl. No.: 406,220

[22] Filed: Sep. 12, 1989

[30] Foreign Application Priority Data

Sep. 21, 1988 [GB] United Kingdom ............... 8822170

[51] Int. Cl.$^5$ .................. C07D 471/04; A61K 31/455
[52] U.S. Cl. .................... 514/303; 546/118; 546/14
[58] Field of Search .................. 546/118, 14; 514/303

[56] References Cited

FOREIGN PATENT DOCUMENTS 0079083 5/1983 European Pat. Off. .
0125803 11/1984 European Pat. Off. .

Primary Examiner—Jane T. Fan
Attorney, Agent, or Firm—Peter C. Richardson; J. Trevor Lumb; James M. McManus

[57] ABSTRACT

The invention provides compounds of the formula

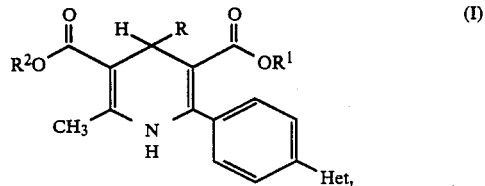

and pharmaceutically acceptable salts thereof, wherein
R is phenyl substituted by halo;
$R^1$ is $C_1$–$C_4$ alkyl;
is hydrogen, $C_5$–$C_7$ cycloalkyl, benzyl or $C_1$–$C_4$ alkyl, said $C_1$–$C_4$ alkyl group being optionally substituted by cyano, trimethylsilyl or $C_1$–$C_3$ alkoxy; and
"Het" is

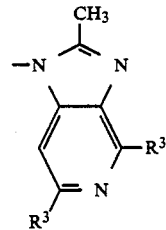

wherein $R^3$ is hydrogen or methyl.

The compounds are useful in the treatment of allergic, inflammatory and hypersecretory conditions, and circulatory shock, stroke and thrombosis.

6 Claims, No Drawings

1,4-DIHYDROPYRIDINE DERIVATIVES

BACKGROUND OF THE INVENTION

This invention relates to dihydropyridines, specifically to certain 4-aryl-1,4-dihydropyridine-5-carboxylic acids and esters thereof, which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents (see for example EP-A-100189). However the compounds of the present invention are potent and selective antagonists of Platelet Activating Factor (PAF) and as such they have clinical utility in quite different areas, such as for treating allergic and inflammatory conditions, e.g. asthma and arthritis respectively.

Platelet Activating Factor (1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic response. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This, coupled with evidence showing that circulating PAF levels are increased by endotoxin infusion indicate that PAF is a prime mediator in certain forms of shock. Intravenous infusion of PAF at doses of 20–200 pmol kg$^{-1}$ min$^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, should be of value in the treatment of any of the above conditions.

SUMMARY OF THE INVENTION

According to the present invention there are provided compounds of the formula:

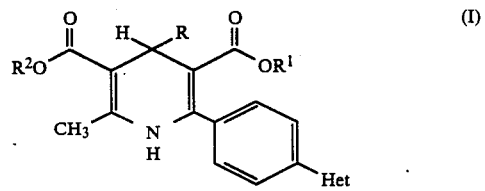

and the pharmaceutically acceptable acid addition salts thereof,
wherein
R is phenyl substituted by either chloro or bromo;
$R^1$ is $C_1$–$C_4$ alkyl;
$R^2$ is hydrogen, $C_5$–$C_7$ cycloalkyl, benzyl or $C_1$–$C_4$ alkyl, said $C_1$–$C_4$ alkyl group being optionally substituted by cyano, trimethylsilyl, or $C_1$–$C_3$ alkoxy; and
"Het" is a group of the formula

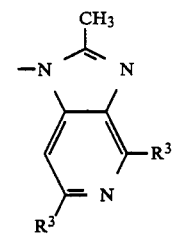

wherein $R^3$ is hydrogen or methyl.

The preferred compounds are those wherein R is 2-chlorophenyl and $R^1$ is ethyl. Especially preferred are the compounds where $R^2$ is methyl and $R^3$ is hydrogen and where $R^2$ is methoxyethyl and $R^3$ is hydrogen.

Also within the scope of the present invention is a method for treating an allergic or inflammatory disease in a human being which comprises administering to said human being an antiallergic or antiinflammatory effective amount of a compound of formula (I) wherein R, $R^1$ and Het are as previously defined and $R^2$ is benzyl, cycloalkyl of five to seven carbon atoms or alkyl of one to four carbon atoms optionally substituted by alkoxy of one to three carbon atoms.

The pharmaceutically acceptable acid addition salts of the compounds of formula (I) are those formed from acids which form non-toxic acid addition salts, for example, the hydrochloride, hydrobromide, sulphate or bisulphate, phosphate or hydrogen phosphate, acetate, citrate, fumarate, gluconate, lactate, maleate, succinate, tartrate, methanesulphonate, benzenesulphonate and p-toluenesulphonate.

The compounds of formula (I) contain at least one asymmetric centre and will therefore exist as one or more pairs of enantiomers, and such individual enantiomers or individual pair of enantiomers may be separable by physical methods, e.g. by fractional crystallization, H.P.L.C. or chromatography of the parent compounds or of a suitable salt or derivative thereof. Alternatively, particular stereoisomers may be prepared using the corresponding stereoisomers of the precursors used in the preparation of compounds of the invention. The invention includes all the stereoisomers of the compounds of formula (I), whether separated or not.

DETAILED DESCRIPTION OF THE INVENTION

The 3,5-diesters of the formula (I) (i.e., the compounds in which $R^2$ is other than hydrogen) may be prepared by the following methods:

(1) According to the Hantzsch synthesis as illustrated by the following reaction scheme:

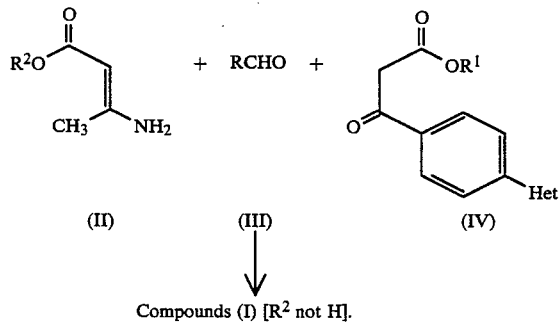

wherein R, $R^1$ and "Het" are as defined for formula (I).

In a typical procedure, the 3-aminocrotonate ester (II), the aldehyde (III) and the β-ketoester (IV) are heated together at from 50° to 120° C., preferably under reflux, in a suitable organic solvent, e.g. a $C_1$–$C_4$ alkanol such as ethanol, and preferably under a nitrogen atmosphere. Optionally a small amount of a lower alkanoic acid, e.g. acetic acid, is present to neutralise the solution. The product of the formula (I) can then be isolated and purified by conventional procedures.

Alternatively, in a modification of the above procedure, the β-ketoester (IV) and the aldehyde (III) are first reacted together, typically by stirring a slight excess of the β-ketoester with the aldehyde at room temperature in a suitable organic solvent, e.g. isopropyl alcohol, optionally containing piperidine as a catalyst, to give an intermediate compound of formula (V):

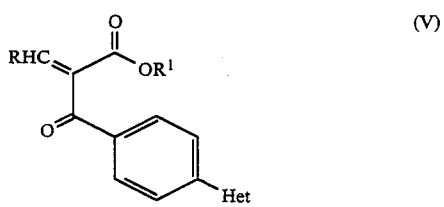

If desired, the intermediate compound (V) may be separated, for example by evaporating the reaction mixture to produce an oil, triturating the oil with water, and purifying the solid product obtained by filtration and recrystallisation. The compound of formula (V) may then be reacted with the 3-aminocrotonate ester (II), typically by heating the compounds together at from 50° to 120° C., preferably under reflux, in a suitable organic solvent, e.g. a $C_1$–$C_4$ alkanol, and preferably under a nitrogen atmosphere, to produce the compound of the formula (I) which again can be isolated and purified by conventional methods.

The β-ketoesters (IV) are either known compounds or can be prepared by the following methods:

(i) The β-ketoesters (IV) may be prepared by a Blaise reaction based on a modification of the literature method according to S. M. Hannick, Y. Kishi, *J. Org. Chem.*, 1983, 48, 3833, as illustrated by the following reaction sequence:

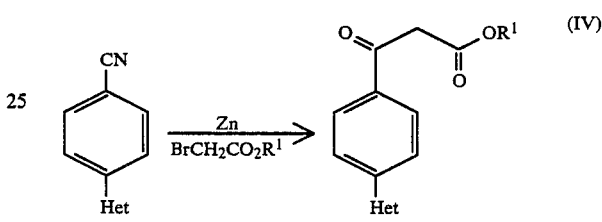

In a typical procedure, the cyano compound is added to a suspension of zinc dust and a few drops of the appropriate bromoacetate in an inert solvent, such as tetrahydrofuran, under nitrogen. The mixture is heated under reflux and further aliquots of the appropriate bromoacetate are added. On completion of the reaction and after cooling, aqueous potassium carbonate is added. After filtration, the filtrate is treated with dilute hydrochloric acid or with 20% aqueous trifluoroacetic acid and a suitable organic solvent such as dichloromethane is added. The reaction mixture is then neutralised and the β-ketoester (IV) isolated and purified by conventional procedures.

The cyano compounds are either known compounds or may be prepared by conventional methods in accordance with literature precedents as illustrated in the Preparations section.

(ii) An alternative method for preparing certain β-ketoesters (IV) is illustrated by the following reaction sequence:

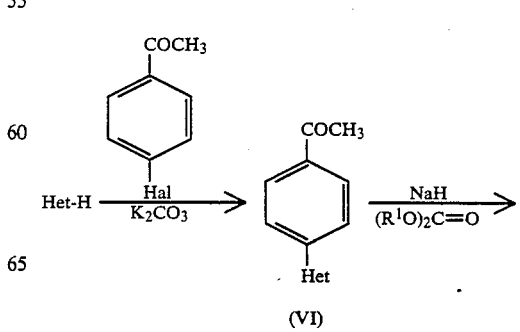

-continued

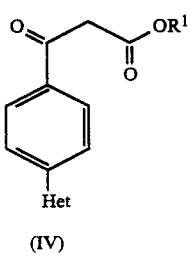

(IV)

wherein "Hal" is halo, preferably fluoro.

Optionally, a copper/cuprous bromide catalyst may be added in the first stage of this sequence, and, in this particular process variant, "Hal" is preferably bromo. In a typical procedure, a mixture of the compound of the formula "Het-H", p-bromoacetophenone, copper bronze, cuprous bromide and anhydrous potassium carbonate in a suitable solvent such as dry N-methylpyrrolidinone, is heated at about 150° C. under an inert atmosphere. The intermediate ketone (VI) obtained is isolated and purified by conventional procedures, and is then added to a suspension of sodium hydride in a suitable dry solvent, such as tetrahydrofuran, under nitrogen. The appropriate dialkyl carbonate is added and the resultant mixture heated under reflux for a suitable period of time. Alternatively, the dialkyl carbonate may itself be used as the solvent. The β-ketoester (IV) obtained is isolated and purified by conventional procedures.

The aldehydes of formula (III) and the 3-aminocrotonate esters of formula (II) are either known compounds or can be prepared by conventional methods in accordance with literature precedents.

(2) Alternatively, the 3,5-diesters of the formula (I) may be prepared by esterification of the corresponding 5-carboxylic acids of the formula (IA) with an alcohol of the formula $R^2OH$.

The esterification is preferably carried out via an "activated ester" derivative of compound (IA).

The preferred esterification technique is illustrated by the following scheme:

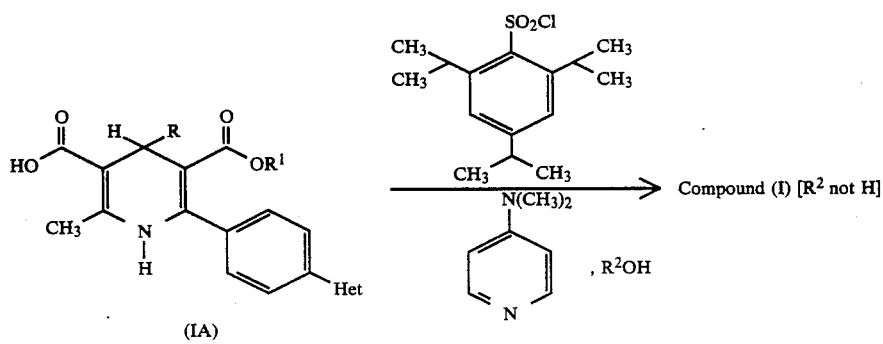

wherein R, $R^1$ and "Het" are as described for formula (I).

In a typical procedure, a mixture of the compound (IA), 2,4,6-triisopropylbenzenesulphonyl chloride and 4-(N,N-dimethylamino)pyridine is stirred at room temperature in a suitable organic solvent, e.g. dichloromethane, for several hours and the alcohol of the formula $R^2OH$ is then added. The 3,5-diester of the formula (I) can then be isolated by conventional procedures.

In an alternative procedure, compound (IA) is first reacted with 1-hydroxybenzotriazole in the presence of a suitable dehydrating agent, e.g. 1,3-dicyclohexylcarbodiimide, and in a suitable organic solvent, e.g. dichloromethane, to form an intermediate "activated ester". Further reaction in situ with the alcohol of the formula $R^2OH$ provided the required product (I).

The 5-carboxylic acids of the formula (IA), wherein R, $R^1$ and "Het" are as previously defined for formula (I), which are not only PAF antagonists but are also useful as intermediates in method (2), may be conveniently prepared by the following methods:

(A) By basic hydrolysis of a compound of the formula:

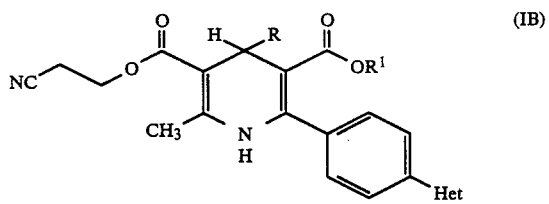

wherein R, $R^1$ and "Het" are as defined for formula (I).

The hydrolysis is typically carried out using a suitable base, e.g. sodium or potassium hydroxide, at about room temperature and in a suitable solvent, e.g. aqueous dioxane. The compound of the formula (IA) can then be isolated and purified by conventional procedures. The compound (IB) is conveniently prepared by the Hantzsch synthesis (Method (1)) previously described; or (B) By reacting a compound of the formula:

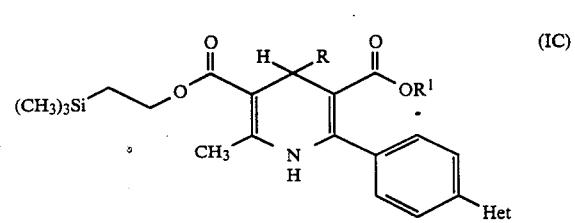

wherein R, $R^1$ and "Het" are as defined for formula (I), with a suitable fluoride ion source, e.g. tetra-n-butylammonium fluoride, and in a suitable solvent, e.g. tetrahydrofuran. The compound of the formula (IA) can then be isolated by conventional procedures.

The compound (IC) is conveniently prepared by the Hantzsch synthesis (Method (1)) previously described.

When the compound of the formula (IB) has one asymmetric centre, the mixture of (+)- and (−)-isomers of the cyanoethyl ester (IB) produced by the Hantzsch synthesis may be conveniently separated by the formation and resolution of suitable diastereoisomeric salt forms, followed by regeneration of the resolved compounds (IB). In the preferred procedure, a salt is formed with the (+)- or (−)-isomer, as appropriate, of 4-(2,4-dichlorophenyl)-5,5-dimethyl-2-hydroxy-1,3,2-dioxaphosphorinane-2-oxide, and fractional recrystallisation of the mixture of diastereoisomeric salts obtained provides a single resolved diastereoisomeric salt (a similar method to that described by W. den Hoeve, H. Wynberg, *J. Org. Chem.*, 50, 4508 [1985]). This may be converted to the corresponding (+)- or (−)-isomer of the free cyanoethyl ester (IB) by treatment with a suitable base, e.g. sodium carbonate.

Hydrolysis of a resolved ester (IB) (see Method (A)) provides a resolved 5-carboxylic acid (IA) which may be used to prepare a resolved 3,5-diester (I) (i.e. $R^2$ not H) by Method (2) previously described.

All of the above reactions are conventional and appropriate reagents and reaction conditions for their performance and procedures for isolating the desired products will be well known to those skilled in the art, in accordance with literature precedents and by reference to the Examples and Preparations hereto.

Pharmaceutically acceptable acid addition salts are readily prepared by mixing solutions containing equimolar amounts of the free base and the desired acid. The salt generally precipitates from solution and is collected by filtration, or is recovered by evaporation of the solvent.

The activity of the compounds of the formula (I) is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 µg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection, or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test, airways resistance and dynamic lung compliance are calculated from recordings of airflow and transpleural pressure and calculation of tidal volume. The bronchoconstriction induced by PAF (100 ng/kg) is determined. One hour after the initial dose of PAF, the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range from 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus, in a further aspect, the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt or composition thereof, for use as a medicament.

The invention further provides the use of a compound of the formula (I), or of a pharmaceutically acceptable salt or composition thereof, for the manufacture of a medicament for the treatment of allergic, inflammatory and hypersecretory conditions and circulatory shock, stroke and thrombosis.

The invention yet further provides a method of treating an animal (including a human being) to cure or prevent an allergic, inflammatory or hypersecretory condition, or circulatory shock, stroke or thrombosis, which comprises administering to said animal or human being, an effective amount of a compound of the formula (I), or a pharmaceutically acceptable salt or composition thereof.

The following Examples illustrate the invention:

EXAMPLE 1

(±)-4-(2-Chlorophenyl)-1,4-dihydro-3-ethoxycarbonyl-5-methoxy-carbonyl-6-methyl-2-[4-(2-methylimidazo[4,5-c]pyridin-1-yl)-phenyl]pyridine

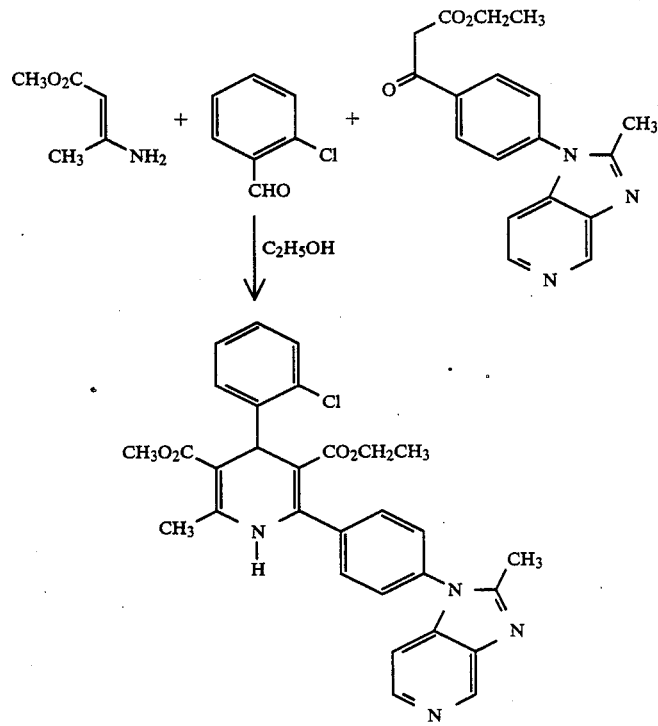

A mixture of ethyl 4'-(2-methylimidazo[4,5-c]pyridin-1-yl)benzoylacetate (see Preparation 1) (323 mg, 1.0 mmol), 2-chlorobenzaldehyde (141 mg, 1.0 mmol) and methyl 3-aminocrotonate (115 mg, 1.0 mmol) in absolute ethanol (4 ml) was heated under reflux under a nitrogen atmosphere for 8 hours. The solution was cooled and concentrated under reduced pressure. The residual gum was purified by flash chromatography on silica gel eluting with 5% diethylamine/ethyl acetate. The product-containing fractions were combined, concentrated under reduced pressure and the residue was suspended in dry ether (5 ml) then stirred overnight. The solid obtained was filtered off and dried in vacuo at 70° C. to give the title compound, (248 mg), m.p. 226°–227° C.

Analysis %: Found: C,66.29; H,4.92; N,10.21; $C_{30}H_{27}ClN_4O_4$ requires: C,66.36; H,5.01; N,10.32.

EXAMPLES 2 to 6

The following racemic compounds were made by similar methods to that of Example 1 using the appropriate 3-aminocrotonate ester, substituted benzaldehyde and β-ketoester derivatives.

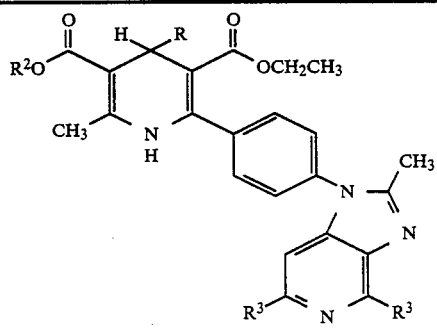

| Example No. | R | $R^2$ | $R^3$ | m.p. (°C.) | Analysis % |
|---|---|---|---|---|---|
| 2 | 2-Cl-C6H4 | C6H5CH2— | H | 114–120 | Found: C, 68.40; H, 5.06; N, 9.47; $C_{36}H_{31}ClN_4O_4$ requires: C, 69.84; H, 5.05; N, 9.05.# |

-continued

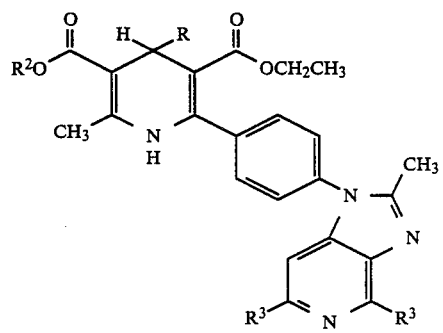

| Example No. | R | R² | R³ | m.p. (°C.) | Analysis % |
|---|---|---|---|---|---|
| 3 | 2-chlorophenyl | cyclohexyl | H | 162–164 | Found: C, 68.62; H, 5.92; N, 9.09; $C_{35}H_{35}ClN_4O_4$ requires: C, 68.79; H, 5.77; N, 9.17. |
| 4 | 2-chlorophenyl | $(CH_3)_3C-$ | H | 194–197 | Found: C, 67.16; H, 5.75; N, 9.59 $C_{33}H_{33}ClN_4O_4$ requires: C, 67.74; H, 5.69; N, 9.58. |
| 5 | 2-chlorophenyl | $(CH_3)_3SiCH_2CH_2-$ | H | 103–105 | Found: C, 64.51; H, 6.06; N, 8.72; $C_{34}H_{37}ClN_4O_4Si\cdot\tfrac{1}{4}CH_3CO_2C_2H_5$ requires: C, 64.55; H, 6.04; N, 8.60. |
| 6 | 2-bromophenyl | $CH_3OCH_2CH_2-$ | $CH_3$ | 131–133 | Found: C, 60.67; H, 5.33; N, 8.57; $C_{34}H_{35}BrN_4O_5\cdot\tfrac{1}{2}H_2O$ requires: C, 61.08; H, 5.43; N, 8.38. |

¹H-NMR (300 MHz. CDCl₃): δ=0.98(3H, t, J=8Hz), 2.42(3H, s), 2.61(3H, s), 3.92(2H, q, J=8Hz), 5.15(2H, q, J=9.6Hz), 5.62(1H, s), 6.06(1H, s), 7.09(1H, d, J=7Hz), 7.17(1H, d, J=7Hz), 7.28(7H, m), 7.44(2H, d, J=7Hz), 7.51(1H, d, J=8Hz), 7.62(2H, d, J=7Hz), 8.37(1H, d, J=7Hz), 9.07(1H, s)p.p.m.

EXAMPLE 7

(±)-4-(2-Chlorophenyl)-5-(2-cyanoethoxycarbonyl)-1,4-dihydro-3-ethoxycarbonyl-6-methyl-2-[4-(2-methylimidazo[4,5-c]pyridin-1-yl)phenyl]pyridine

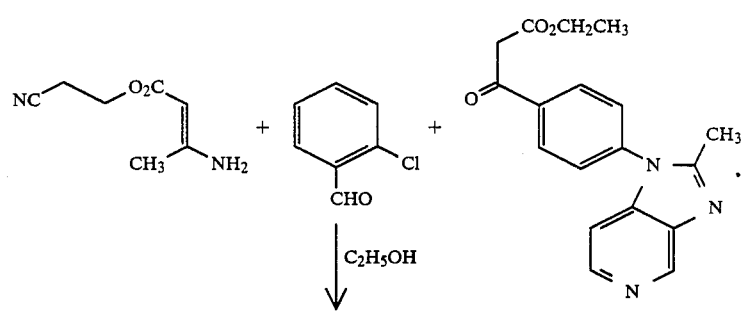

-continued

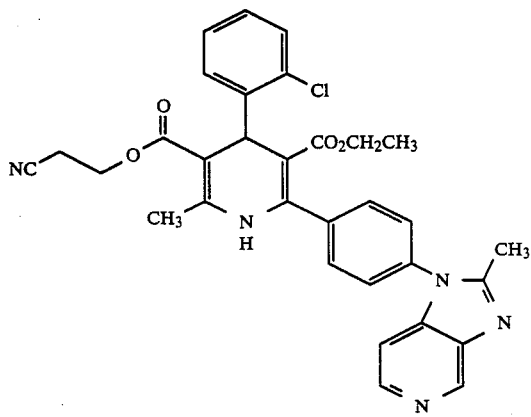

20

A mixture of ethyl 4'-(2-methylimidazo[4,5-c]pyridin-1-yl)benzoylacetate (see Preparation 1) (7.50 g, 23.1 mmol), 2-chlorobenzaldehyde (3.25 g, 23.1 mmol) and 2-cyanoethyl 3-aminocrotonate (3.56 g, 23.1 mmol) in ethanol (60 ml) were reacted together as described in Example 1. Purification of the crude product by flash chromatography (eluting with ethyl acetate/diethylamine, 19:1), followed by trituration with ether gave the title compound as an off-white solid, (5.875 g, 44%), m.p. 177°–179° C.

Analysis %: Found: C,65.59; H,4.81; N,11.89; $C_{32}H_{28}ClN_5O_4$ requires: C,66.03; H, 4.85; N,12.03.

EXAMPLE 8

(−)-4-(2-Chlorophenyl)-5-(2-cyanoethoxycarbonyl)-1,4-dihydro-3-ethoxycarbonyl-6-methyl-2-[4-(2-methylimidazo[4,5-c]pyridin-1-yl)phenyl]pyridine A solution of the (±)-cyanoethyl ester of Example 7 (2.340 g, 4.02 mmol) in hot methanol (20 ml) was treated with (−)-4-(2,4-dichlorophenyl)-5,5-dimethyl-2-hydroxy-1,3,2-dioxaphosphorinane-2-oxide (W. den Hoeve, H. Wynberg, *J. Org. Chem.*, 1985, 50, 4508) (1.250 g, 4.02 mmol) to form a solution of the mixture of diastereoisomeric salts. The solvent was evaporated and crystallisation was induced by triturating with ethyl acetate and cooling.

The resulting mixture of diastereoisomeric salts was recrystallised from methanol/toluene to give the (−)-cyanoethyl ester (−)-salt (207 mg). The mother liquors were concentrated under reduced pressure and recrystallised from dichloromethane/ethyl acetate to give a further 350 mg of the (−)-cyanoethyl ester (−)-salt, m.p. 141°–144° C., $[\alpha]_{436}^{25} = -36.9°$ (c=0.52, ethanol).

$^1$H-NMR (500 MHz; CDCl$_3$) showed that the diastereoisomeric excess was 92%.

Analysis %: Found: C,56.91; H,4.70; N,7.72; $C_{43}H_{41}Cl_3N_5O_8P.H_2O$ requires: C,56.68; H,4.76; N,7.69.

Treatment of this salt with base (Na$_2$CO$_3$) and extraction with dichloromethane gave the title compound, (271 mg), m.p. 177°–179° C. (ethyl acetate), $[\alpha]_{589}^{25} = -38.2°$ (c=0.28, ethanol).

Analysis %: Found: C,65.75; H,4.86; N,12.02; $C_{32}H_{28}ClN_5O_4$ requires: C,66.03; H,4.85; N,12.03.

EXAMPLE 9

(+)-4-(2-Chlorophenyl)-5-(2-cyanoethoxycarbonyl)-1,4-dihydro-3-ethoxycarbonyl-6-methyl-2-[4-(2-methylimidazo[4,5-c]pyridin-1-yl)phenyl]pyridine By a similar method to Example 8, the (±)-cyanoethyl ester of Example 7 (3.492 g, 6.0 mmol) was treated with (+)-4-(2,4-dichlorophenyl)-5,5-dimethyl-2-2-hydroxy-1,3,2-dioxaphosphorinane-2-oxide (1.866 g, 6.0 mmol), and the resulting mixture of diastereoisomeric salts was recrystallised from methanol/toluene and then dichloromethane/ethyl acetate to give the optically pure (+)-cyanoethyl ester (+)-salt (2.30 g). The salt was decomposed with sodium carbonate as described in Example 8, to yield the title compound, (735 mg), m.p. 177°–179° C. (ethyl acetate), $[\alpha]_{589}^{25} = +38.9°$ (c=0.27, ethanol).

Analysis %: Found: C,66.02; H,4.94; N,12.20; $C_{32}H_{28}ClN_5O_4$ requires: C,66.03; H,4.85; N,12.03.

EXAMPLE 10

(±)-4-(2-Chlorophenyl)-1,4-dihydro-3-ethoxycarbonyl-6-methyl-2-[4-(2-methylimidazo[4,5-c[pyridin-1-yl)phenyl]pyridine-5-carboxylic acid

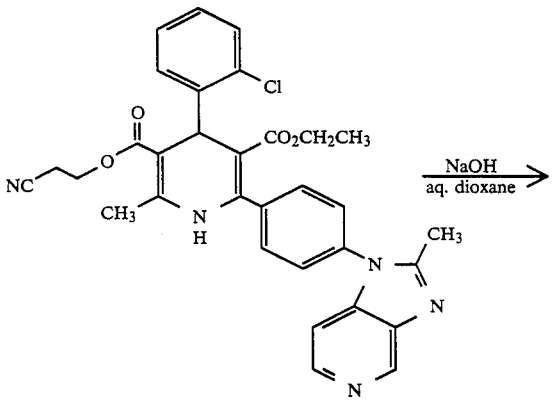

-continued

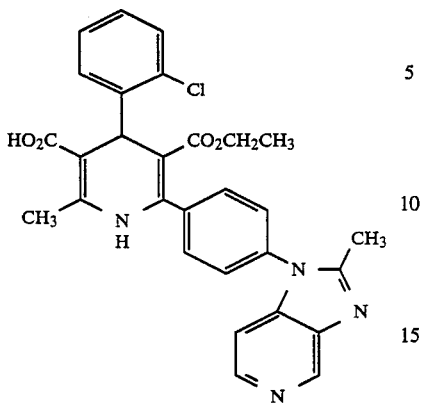

(±)-4-(2-Chlorophenyl)-5-(2-cyanoethoxycarbonyl)-1,4-dihydro-3-ethoxycarbonyl-6-methyl-2-[4-(2-methylimidazo[4,5-c]pyridin-1-yl)phenyl]pyridine (see Example 7) (2.91 g, 5 mmol) was added to a solution of sodium hydroxide (600 mg, 15 mmol) in aqueous dioxane (1:3, 90 ml) at room temperature with stirring. After 1 hour, the mixture was treated with hydrochloric acid (15 ml, 1.0M) and concentrated under reduced pressure. The residue was suspended in water, the solid filtered off, washed with water, and dried in vacuo at 70° C. to give the title compound, (2.548 g), m.p. 206°–208° C.

Analysis %: Found: C,64.23; H,4.82; N,10.57; $C_{29}H_{25}ClN_4O_4.\frac{2}{3}$ $H_2O$ requires: C,64.38; H,4.91; N,10.36.

EXAMPLE 11

(−)-4-(2-Chlorophenyl)-1,4-dihydro-3-ethoxycarbonyl-6-methyl-2-[4-(2-methylimidazo[4,5-c]pyridin-1yl)-phenyl]pyridine-5-carboxylic acid A mixture of the (−)-cyanoethyl ester of Example 8 (271 mg, 0.466 mmol) and aqueous sodium hydroxide (2.54 ml, 0.55M, 1.40 mmol) in dioxane (7.5 ml) was stirred at room temperature under nitrogen for 1 hour. Hydrochloric acid (1.40 ml, 1M, 1.40 mmol) was added dropwise, and the mixture was concentrated under reduced pressure. The resulting yellow solid was suspended in water, filtered off, and dried in vacuo, to give the title compound, (200 mg, 81%).

$^1$H-NMR (300 MHz, DMSO-d$_6$): δ=0.8 (3H, t, J=7 Hz), 2.28 (3H, s), 2.50 (3H, s), 2.71 (2H, q, J=7 Hz), 5.37 (1H, s), 7.11 (1H, d, J=6 Hz), 7.15 (1H, m), 7.28 (2H, m), 7.49 (1H, m), 7.53 (2H, d, J=8 Hz), 7.63 (2H, d, J=8 Hz), 8.34 (1H, d, J=6 Hz), 8.93 (1H, s), 9.09 (1H, s) p.p.m.

EXAMPLE 12

(+)-4-(2-Chlorophenyl)-1,4-dihydro-3-ethoxycarbonyl-6-methyl-2-[4-(2-methylimidazo[4,5-c]pyridin-1-yl]phenyl)pyridine-5-carboxylic acid The (+)-cyanoethyl ester of Example 9 (531 mg, 0.91 mmol) was converted into the title compound by the method described for Example 11. The title compound was obtained as a yellow solid, (340 mg, 71%), $[\alpha]_{589}^{25}$= +96.9° (c=0.295, ethanol).

EXAMPLE 13

(±)-4-(2-Chlorophenyl)-1,4-dihydro-3-ethoxycarbonyl-5-(2-methoxyethoxycarbonyl)-6-methyl-2-[4-(2-methylimidazo[4,5-c]pyridin-1-yl)phenyl]pyridine

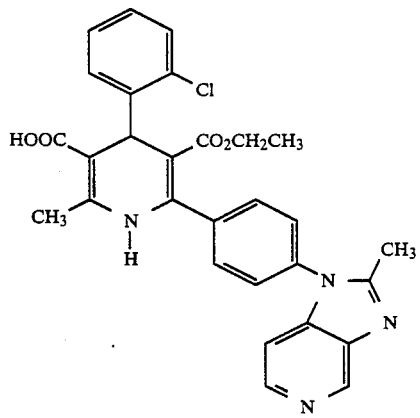

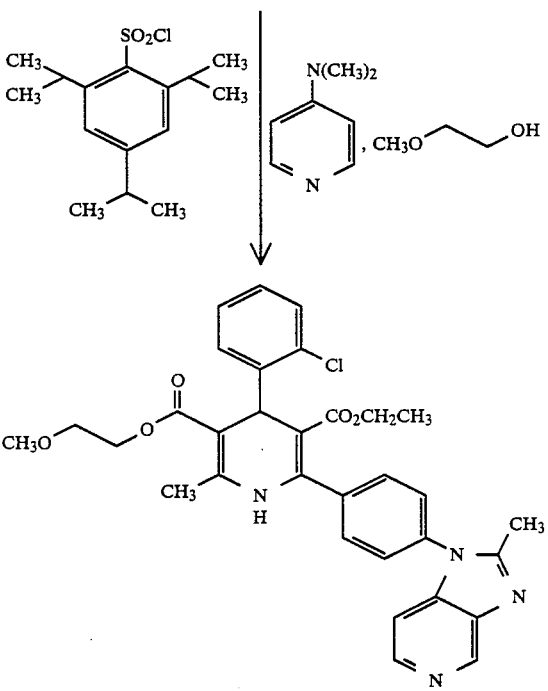

A mixture of (±)-4-(2-chlorophenyl)-1,4-dihydro-3-ethoxycarbonyl-6-methyl-2-[4-(2-methylimidazo[4,5-c]pyridin-1-yl)phenyl]pyridine-5-carboxylic acid (see Example 10) (270 mg, 0.5 mmol), 2,4,6-triisopropylbenzenesulphonyl chloride (377 mg, 1.25 mmol) and 4-dimethylaminopyridine (152 mg, 1.25 mmol) in dry dichloromethane (10 ml) was stirred under a nitrogen atmosphere at room temperature for 3 hours. 2-Methoxyethanol (1.0 ml) was added and the solution was stirred at room temperature for 20 hours. The mixture was concentrated under reduced pressure, the residue was dissolved in excess 0.5M hydrochloric acid and washed with ether (2×30 ml). The aqueous solution was basified with excess saturated aqueous sodium bicarbonate and extracted with dichloromethane (4×30 ml). The combined organic extracts were dried (MgSO$_4$), concentrated, and purified by flash chromatography on silica gel (eluting with 10:1 ethyl acetate/triethylamine) to give, after combination and evaporation of appropriate fractions, the title compound, (93 mg), m.p. 195°–196° C.

Analysis %: Found: C,65.38; H,5.35; N,9.66; C$_{32}$H$_{31}$ClN$_4$O$_5$ requires: C,65.47; H, 5.32; N,9.54.

The following Preparations illustrate the preparation of intermediates used in the preceding Examples.

PREPARATION 1

Ethyl 4'-(2-methylimidazo[4,5-c]pyridin-1yl)benzoylacetate

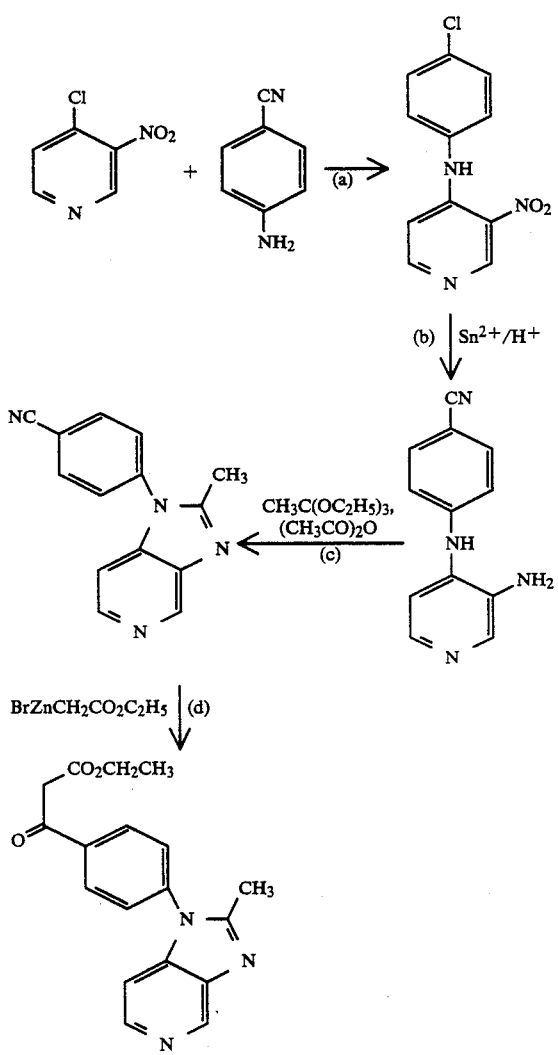

(a) 4-[N-(4-Cyanophenyl)amino]-3-nitropyridine

According to the method of *J. C. S. Perkin Trans. I,* 1979, 135, p-cyanoaniline (6.894 g, 58.4 mmol) was added to a solution of 4-chloro-3-nitropyridine (9.26 g, 58.4 mmol) in ethanol (200 ml) and the mixture was stirred at room temperature for 18 hours. The resulting yellow suspension was poured into 500 ml of ice-cold dilute ammonia and filtered. The solid was treated with 150 ml of boiling ethanol, cooled in ice, and filtered to give the title compound as a bright yellow powder, (12.15 g), m.p. 210°–211° C.

$^1$H-NMR (CDCl$_3$): δ=7.15 (1H, d, J=9 Hz), 7.79 (2H, d, J=9 Hz), 8.43 (1H, d, J=6 Hz), 9.36 (1H, s) 9.80 (1H, br, s) p.p.m.

(b) 3-Amino-4-[N-(4-cyanophenyl)amino]pyridine

According to a modification of the method of Pharm. Helv. Acta, 1975, 50, 188 , tin (II) dichloride dihydrate (56.4 g, 250 mmol) was added to a suspension of 4-[N-(4-cyanophenyl)amino]-3-nitropyridine (see part (a)) (12.0 g, 50 mmol) in 2N aqueous hydrochloric acid (35 ml), water (150 ml) and ethanol (75 ml) and the resulting mixture was heated to reflux for 10 minutes under nitrogen. The mixture was cooled in ice, poured into ice-cold 2N aqueous sodium hydroxide (400 ml) and filtered. The creamy-coloured solid was washed with 2N aqueous sodium hydroxide and water, and then dried in a vacuum desiccator to provide the title compound, (9.31 g), which gradually turns reddish brown on exposure to light and air.

$^1$H-NMR (CDCl$_3$): δ=3.52 (2H, br s), 6.04 (1H, br s), 7.03 (2H, d, J=9 Hz), 7.59 (2H, d, J=9 Hz), 8.07 (1H, m), 8.20 (1H, s) p.p.m.

(c) 1-(4-Cyanophenyl)-2-methylimidazo[4,5-c]pyridine

A mixture of 3-amino-4-[N-(4-cyanophenyl)amino]-pyridine (see part (b)) (9.31 g, 44.3 mmol), triethyl orthoacetate (40 ml) and acetic anhydride (30 ml) was heated at reflux for 2 hours under nitrogen, cooled, then concentrated under reduced pressure. The brown residue was dissolved in 1M hydrochloric acid and washed with ethyl acetate (200 ml). The aqueous layer was rendered basic with saturated aqueous ammonia and extracted with dichloromethane (3×200 ml). The combined extracts were washed with water, dried (MgSO$_4$) and concentrated to give the title compound (6.5 g), as a brown solid.

$^1$H-NMR (CDCl$_3$): δ=2.61 (3H, s), 7.13 (1H, d, J=6 Hz), 7.58 (2H, d, J=9 Hz), 7.98 (2H, d, J=9 Hz), 8.45 (1H, d, J=6 Hz), 9.11 (1H, s) p.p.m.

(d) Ethyl 4'-(2-methylimidazo[4,5-c]pyridin-1-yl)benzoylacetate

Zinc dust (894 mg, 13.7 mmol) was suspended in dry THF (3 ml) under nitrogen and sonicated at room temperature for 10 minutes. Ethyl bromoacetate (2 drops) was added and the mixture was heated under reflux for 5 minutes. A solution of 1-(4-cyanophenyl)-2-methylimidazo[4,5-c]pyridine (640 mg, 2.74 mmol) in dry THF (6 ml) was added and the mixture was refluxed for 5 minutes. A solution of ethyl bromoacetate (1.822 g, 10.94 mmol) in dry THF (2 ml) was added dropwise over 1 hour at reflux and, after a further 10 minutes, the mixture was allowed to cool to room temperature. 50% Aqueous potassium carbonate (1 ml) was added and the mixture was stirred for 45 minutes at room temperature then filtered through "Arbocel" (Trade Mark) filter aid, washing with THF. The filtrate was concentrated under reduced pressure to give a yellow gum. This material was treated with a mixture of 20% aqueous trifluoroacetic acid (10 ml) and dichloromethane (50 ml) and stirred at room temperature for 15 minutes. The mixture was neutralised by the addition of saturated aqueous sodium bicarbonate and then extracted with dichloromethane (2×30 ml). The combined extracts were dried (MgSO$_4$), concentrated under reduced pressure and the crude product was purified by flash chromatography on silica gel (eluting with 10% changing to 20% methanol/ethyl acetate) to give, after combination and evaporation of appropriate fractions, the title compound (480 mg, 54%), as a yellow gum.

This material was rechromatographed (eluting with 7:1 ethyl acetate/methanol) to give, after combination and evaporation of appropriate fractions, a white solid, m.p. 111°–112° C. (ethyl acetate).

¹H-NMR (CDCl₃): δ=1.32 ((3H, t, J=6 Hz), 2.61 (3H, s), 4.09 (2H, s), 4.28 (2H, q, J=6 Hz), 7.16 (1H, d, J=6 Hz), 7.55 (2H, d, J=9 Hz), 8.23 (2H, d, J=9 Hz), 8.46 (1H, d, J=6 Hz), 9.09 (1H, s) p.p.m.

PREPARATION 2

Ethyl 4′-(2,4,6-trimethylimidazo[4,5-c]pyridin-1-yl)benzoylacetate the pale buff crystals obtained were filtered off, washed with a little water, and sucked dry to give 2,6-dimethyl-4(1H)-pyridone nitrate salt, (46.79 g, 59%). This material was added in portions to a mixture of fuming sulphuric acid (23 ml) and fuming nitric acid (31 ml) at room temperature, and the mixture was heated to 100° C. and held at this temperature for 5.5 hours. The mixture was poured onto ice and neutralised with saturated aqueous potassium carbonate. The pale yellow solid which precipitated was filtered off and extracted with boiling isopropanol in a Soxhlet extractor. The isopropanol was removed under reduced pressure to give the title compound, (26.5 g, 63%).

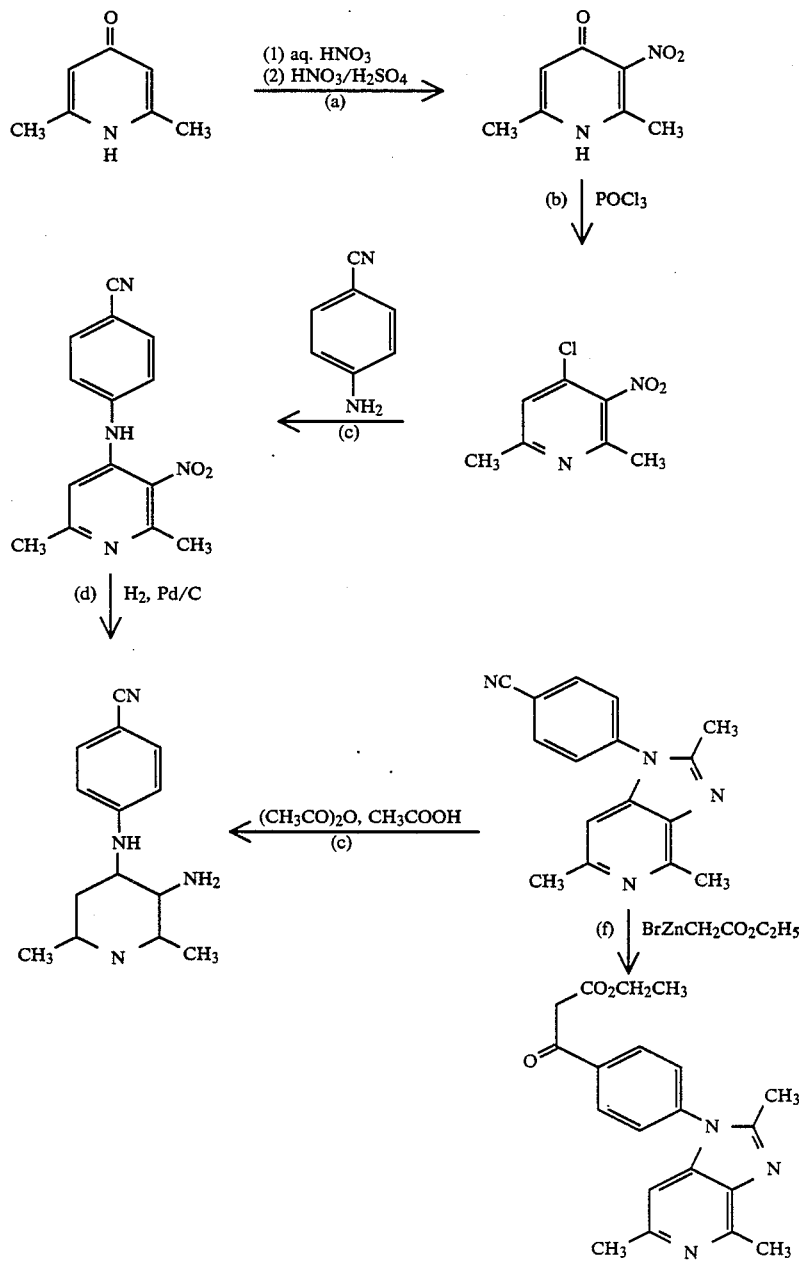

(a) 2,6-Dimethyl-3-nitro-4(1H)-pyridone 2,6-Dimethyl-4(1H)-pyridone (*Chem. Abs.*, 84, 4811x, (1976)) (52.56 g, 0.427 mol) was dissolved in water (100 ml) at 50° C., and fuming nitric acid (40 ml) was added dropwise. The mixture was cooled in ice for 45 minutes, ¹H-NMR (300 MHz, MeOH-d₄): δ=2.38 (3H, s), 2.45 (3H, s), 6.39 (1H, s) p.p.m.

(b) 4-Chloro-2,6-dimethyl-3-nitropyridine

By the method of *Yakugaku Zasshi,* 87, 387 (1967), 2,6-dimethyl-3-nitro-4(1H)-pyridone (see part (a)) (11.23 g, 66.8 mmol) and phosphorus oxychloride (57 ml) were heated together at reflux for 1.5 hours. The excess reagent was removed under reduced pressure, and the residue dissolved in dichloromethane (150 ml). This solution was treated with dilute aqueous sodium bicarbonate until the aqueous layer was at pH7, then the organic phase was separated, dried (MgSO₄) and concentrated under reduced pressure to give the title compound as a pale yellow solid, (9.8 g, 79%). Caution: this compound is a potential skin irritant.

$^1$H-NMR (300 MHz, CDCl$_3$): δ=2.58 (3H, s), 2.61 (3H, s), 7.22 (1H, s) p.p.m.

(c) 4-[N-(4-Cyanophenyl)amino]-2,6-dimethyl-3-nitropyridine

A solution of 4-chloro-2,6-dimethyl-3-nitropyridine (see part (b)) (9.80 g, 52.5 mmol) and 4-aminobenzonitrile (6.20 g, 52.5 mmol) in ethanol (160 ml) was stirred at room temperature for 16 hours. The solvent was removed under reduced pressure and the residue was dissolved in dichloromethane (200 ml) and washed with saturated aqueous sodium bicarbonate (100 ml). The organic phase was dried (MgSO₄) and concentrated under reduced pressure to give a gum which was crystallised by adding ether (100 ml) and sonicating for 5 minutes. The title compound was obtained as a yellow solid which was filtered off and dried in vacuo, (9.80 g, 70%) m.p. 171°–172° C.

$^1$H-NMR (300 MHz, CDCl$_3$): δ=2.49 (3H, s), 2.76 (3H, s), 6.96 (1H, s), 7.35 (2H, d, J 8 Hz), 7.74 (2H, d, J 8 Hz), 8.69 (1H, br s) p.p.m.

(d) 3-Amino-4-[N-(4-cyanophenyl)amino]-2,6-dimethylpyridine

A solution of 4-[N-(4-cyanophenyl)amino]-2,6-dimethyl-3-nitropyridine (see part (c)) (5.00 g, 18.6 mmol) in a mixture of dichloromethane (20 ml) and ethanol (100 ml) was hydrogenated at 20° C. over 10% palladium on charcoal (500 mg) at 138 kPa (20 p.s.i.) for 3 hours. The catalyst was filtered off and the solvents were removed under reduced pressure to give the title compound as a brown solid, (4.20 g, 94%).

$^1$H-NMR (300 MHz, MeOH-d$_4$): δ=2.39 (3H, s), 2.62 (3H, s), 6.98 (1H, s), 7.11 (2H, d, J=8 Hz), 7.62 (2H, d, J=8 Hz) p.p.m.

(e) 1-(4-Cyanophenyl)-2,4,6-trimethylimidazo[4,5-]pyridine

A mixture of 3-amino-4-[N-(4-cyanophenyl)amino]-2,6-dimethylpyridine (see part (d)) (4.20 g, 17.6 mmol), acetic anhydride (12.6 ml) and acetic acid (12.6 ml) was stirred at 100° C. for 16 hours. The excess of reagents was removed under reduced pressure, the residual gum was dissolved in water and the solution was rendered basic by the addition of concentrated aqueous ammonia. The white solid which precipitated was filtered off and dried in vacuo to give the title compound, (4.06 g, 88%), m.p. 260°–262° C.

$^1$H-NMR (300 MHz, CDCl$_3$): δ=2.60 (3H, s), 2.65 (3H, s), 2.90 (3H, s), 6.81 (1H, s), 7.55 (2H, d, J=8 Hz), 7.96 (2H, d, J=8 Hz) p.p.m.

Analysis %: Found: C,73.57; H,5.37; N,21.53; C₁₆H₁₄N₄ requires: C,73.26; H,5.38; N,21.36.

(f) Ethyl 4'-(2,4,6-trimethylimidazo[4,5-c]pyridin-1-yl)benzoylacetate

The title compound was obtained as a gum by a similar method to Preparation 1(d) starting from 1-(4-cyanophenyl)-2,4,6-trimethylimidazo[4,5-c]pyridine (see part (e)).

$^1$H-NMR (300 MHz, CDCl$_3$): δ=1.36 (3H, t, J=6 Hz), 2.59 (3H, s), 2.62 (3H, s), 2.90 (3H, s), 4.09 (2H, q, J=6 Hz), 7.55 (2H, d, J=9 Hz), 7.97 (2H, d, J=9 Hz), 8.21 (1H, s) p.p.m.

We Claim:

1. A compound of the formula

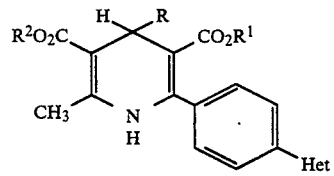

or a pharmaceutically acceptable acid addition salt thereof, wherein R is chlorophenyl or bromophenyl; $R^1$ is alkyl having one to four carbon atoms; $R^2$ is hydrogen, benzyl, cycloalkyl having five to seven carbon atoms or alkyl having one to four carbon atoms optionally substituted by cyano, trimethylsilyl or alkoxy having one to three carbon atoms, and Het is a group of the formula

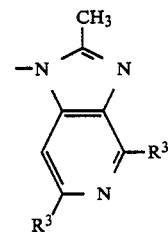

wherein $R^3$ is hydrogen or methyl.

2. A compound of claim 1, wherein R is 2-chlorophenyl and $R^1$ is ethyl.

3. The compound of claim 2, wherein $R^2$ is methyl and $R^3$ is hydrogen.

4. The compound of claim 2, wherein $R^2$ is methoxyethyl and $R^3$ is hydrogen.

5. A method of treating an allergic or inflammatory disease in a human being which comprises administering to said human being an antiallergic or antiinflammatory effective amount of a compound of the formula

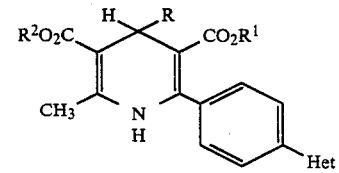

or a pharmaceutically acceptable acid addition salt thereof, wherein R is chlorophenyl or bromophenyl; $R^1$ is alkyl having one to four carbon atoms; $R^2$ is benzyl, cycloalkyl having five to seven carbon atoms or alkyl having one to four carbon atoms optionally substituted by alkoxy having one to three carbon atoms; and Het is a group of the formula

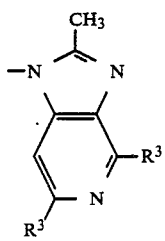

wherein R³ is hydrogen or methyl.

6. A pharmaceutical composition for the treatment of an allergic or inflammatory disease in a human being, which comprises an effective amount a compound of the formula

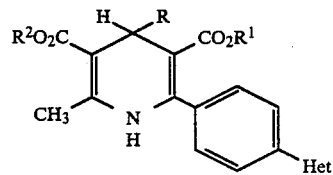

or a pharmaceutically acceptable acid addition salt thereof, wherein R is chlorophenyl or bromophenyl; R¹ is alkyl having one to four carbon atoms; R² is benzyl, cycloalkyl having five to seven carbon atoms or alkyl having one to four carbon atoms optionally substituted by alkoxy having one to three carbon atoms; and Het is a group of the formula

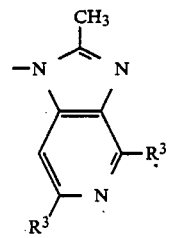

wherein R³ is hydrogen or methyl, together with a pharmaceutically acceptable diluent or carrier.

* * * * *